US011617887B2

(12) United States Patent
Rao et al.

(10) Patent No.: US 11,617,887 B2
(45) Date of Patent: Apr. 4, 2023

(54) SYSTEMS AND METHODS FOR BRAIN STIMULATION FOR RECOVERY FROM BRAIN INJURY, SUCH AS STROKE

(71) Applicants: University of Washington, Seattle, WA (US); Seattle Children's Hospital, Seattle, WA (US)

(72) Inventors: Rajesh P. N. Rao, Seattle, WA (US); Jeffrey G. Ojemann, Seattle, WA (US); Eberhard E. Fetz, Seattle, WA (US); Chet T. Moritz, Seattle, WA (US); Jeffrey Herron, Seattle, WA (US)

(73) Assignee: University of Washington and Seattle Children's Hospital Children's Research Institute, Seattle, WA (US)

( * ) Notice: Subject to any disclaimer, the term of this patent is extended or adjusted under 35 U.S.C. 154(b) by 375 days.

(21) Appl. No.: 16/389,823

(22) Filed: Apr. 19, 2019

(65) Prior Publication Data

US 2019/0321639 A1    Oct. 24, 2019

Related U.S. Application Data

(60) Provisional application No. 62/660,035, filed on Apr. 19, 2018.

(51) Int. Cl.
*A61N 1/00* (2006.01)
*A61N 1/36* (2006.01)
*A61N 1/05* (2006.01)

(52) U.S. Cl.
CPC ....... *A61N 1/36103* (2013.01); *A61N 1/0529* (2013.01); *A61N 1/36025* (2013.01); *A61N 1/36082* (2013.01)

(58) Field of Classification Search
CPC ................................................. A61N 1/36103
(Continued)

(56) References Cited

U.S. PATENT DOCUMENTS 7,010,351 B2    3/2006   Firlik et al.
7,209,787 B2    4/2007   DiLorenzo
(Continued)

FOREIGN PATENT DOCUMENTS

CN    101596338 A    12/2009
CN    106345056 A     1/2017
(Continued)

OTHER PUBLICATIONS

Jackson et al., "Long-term motor cortex plasticity induced by an electronic neural implant," Nature, vol. 444, p. 56-60, Nov. 2, 2006.
(Continued)

*Primary Examiner* — Nicole F Lavert
(74) *Attorney, Agent, or Firm* — Dorsey & Whitney LLP (57) ABSTRACT

Systems and methods for promoting neuroplasticity in a brain of a subject to improve and/or restore neural function are disclosed herein. One such method includes detecting residual movement and/or muscular activity in a limb of the subject, such as a paretic limb. The method further includes generating a stimulation pattern based on the detected movement and/or muscular activity, and stimulating the brain of the subject with the stimulation pattern. It is expected that delivering stimulation based on the detected residual movement and/or muscular activity of the limb will induce neuroplasticity for restoring neural function, such as control of the limb. A second method involves detecting brain signals and delivering contingent stimulation. A third method involves delivering pairs of successive stimulus patterns to two brain sites, controlled either by preprogrammed sequences or contingent on neural or muscular activity or movement.

22 Claims, 7 Drawing Sheets

(58) Field of Classification Search
USPC .......................................................... 607/45
See application file for complete search history.

(56) References Cited

U.S. PATENT DOCUMENTS

| | | | |
|---|---|---|---|
| 7,209,788 | B2 | 4/2007 | Nicolelis et al. |
| 7,460,911 | B2 | 12/2008 | Cosendai et al. |
| 8,401,634 | B2 | 3/2013 | Whitehurst et al. |
| 9,302,103 | B1 | 4/2016 | Nirenberg |
| 9,489,623 | B1 | 11/2016 | Sinyavskiy et al. |
| 2002/0087201 | A1* | 7/2002 | Firlik ................ A61N 1/37514 607/45 |
| 2003/0093129 | A1 | 5/2003 | Nicolelis et al. |
| 2005/0267597 | A1 | 12/2005 | Flaherty et al. |
| 2007/0239211 | A1 | 10/2007 | Lorincz et al. |
| 2008/0045775 | A1 | 2/2008 | Lozano |
| 2009/0306491 | A1 | 12/2009 | Haggers |
| 2009/0306741 | A1 | 12/2009 | Hogle et al. |
| 2010/0003656 | A1 | 1/2010 | Rosellini et al. |
| 2012/0271377 | A1 | 10/2012 | Hagedorn et al. |
| 2013/0035745 | A1* | 2/2013 | Ahmed .............. A61N 1/36103 607/66 |
| 2013/0090706 | A1 | 4/2013 | Nudo et al. |
| 2014/0211593 | A1* | 7/2014 | Tyler ...................... H04B 11/00 367/137 |
| 2014/0358192 | A1 | 12/2014 | Wheeler Moss et al. |
| 2015/0012111 | A1 | 1/2015 | Contreras-vidal et al. |
| 2015/0080746 | A1* | 3/2015 | Bleich .................... G16H 20/30 600/479 |
| 2016/0048753 | A1 | 2/2016 | Sussillo et al. |
| 2016/0129276 | A1 | 5/2016 | Fried et al. |
| 2016/0235323 | A1 | 8/2016 | Tadi |
| 2017/0020448 | A1 | 1/2017 | Williams et al. |
| 2017/0056642 | A1 | 3/2017 | Moffitt et al. |
| 2017/0196513 | A1* | 7/2017 | Longinotti-Buitoni ...................... A61B 5/7278 |
| 2017/0258390 | A1* | 9/2017 | Howard ................. A61B 5/369 |
| 2017/0281946 | A1 | 10/2017 | Katnani |
| 2017/0296048 | A1 | 10/2017 | Lahiri |
| 2017/0325705 | A1* | 11/2017 | Ramos Murguialday ................... A61B 5/1122 |
| 2018/0078770 | A1 | 3/2018 | Rickert et al. |
| 2019/0262612 | A1 | 8/2019 | Rao et al. |
| 2019/0299008 | A1 | 10/2019 | Rao |

FOREIGN PATENT DOCUMENTS

| | | |
|---|---|---|
| KR | 20150136704 A | 12/2015 |
| KR | 20180001408 U | 5/2018 |
| WO | 2014025765 A2 | 2/2014 |
| WO | 2016182947 A1 | 11/2016 |
| WO | 2017100649 A1 | 6/2017 |
| WO | 2017112679 A1 | 6/2017 |
| WO | 2018047164 A1 | 3/2018 |

OTHER PUBLICATIONS

Lucas T et al., "Myo-cortical crossed feedback reorganizes primate motor cortex output," Journal for Neuroscience, 33:5261-5274, 2013.
Nishimura Y. et al., "Spike-timing dependent plasticity in primate corticospinal connections induced during free behavior," Neuron, 80: 1301-1309, 2013.
Seeman S.C. et al., "Paired stimulation for spike-timing dependent plasticity in primate sensorimotor cortex," J. Neuroscience. 37 7: 1935-1949, 2017.
Zanos et al., "The Neurochip-2: An Autonomous Head-Fixed Computer for Recording and Stimulating in Freely Behaving Monkeys," IEEE Transactions on Neural Systems And Rehabilitation Engineering, vol. 19, No. 4, p. 427-435, Aug. 2011.
Zanos et al., "Phase-locked stimulation during cortical beta oscillations produces bidirectional synaptic plasticity in awake monkeys," Current Biology 28, 2515-2526, 2018.

Adkins, D.L. et al., "Motor cortical stimulation promotes synaptic plasticity and behavioral improvements following sensorimotor cortex lesions," ScienceDirect, Experimental Neurology 212 (2008), pp. 14-28.
Allart, E. et al., "Parietomotor connectivity in the contralesional hemisphere after stroke: A paired-pulse TMS study," Clinical Neurophysiology, 128 (2017), pp. 707-715.
Bell, C.J. et al., "Control of a humanoid robot by a noninvasive brain-computer interface in humans," Journal of Neural Engineering 5 (2008), pp. 214-220.
Berger, T.W. et al., "A cortical neural prosthesis for restoring and enhancing memory," Journal of Neural Engineering 8 (2011), 11 pages.
Brown, J. et al., "Motor Cortex Stimulation for the enhancement of recovery from stroke: A prospective, Multicenter safety study," Neurosurgery 58: 2006: 464-473.
Dethier, J. et al., "Design and validation of a real-time spiking neural-network decoder for brain-machine interfaces," Journal of Neural Engineering 10 (2013), 12 pages.
Donoghue, J. et al., "Assistive technology and robotic control using motor cortex ensemble-based neural interface systems in humans with tetraplegia," J. Physical 579.3 (2007), pp. 603-611.
Ezzyat, Y. et al., "Closed-loop stimulation of temporal cortex rescues functional networks and improves memory," Nature Communications (2018) 9:365, 8 pages.
Guggenmos, D. et al., "Restoration of function after brain damage using a neural prosthesis," PNAS, Dec. 24, 2013, vol. 110, No. 52, pp. 21177-21182.
Hamilton, L. et al., "Neural Signal Processing and Closed-loop Control Algorithm Design for an Implanted Neural Recording and Stimulation System," IEEE, 2015, 6 pages.
Houston, B. et al., "Classifier-Based closed-loop deep brain stimulation for essential tremor," IEEE 2017, 5 pages.
International Search Report and Written Opinion in International Application No. PCT/US2017/044012, dated Oct. 3, 2017, 8 pages.
Jure, F. et al., "BCI-FES system for neuro-rehabilitation of stroke patients," Journal of Physics 705 (2016, 9 pages.
Levy, R. et al., "Epidural Electrical Stimulation for stroke rehabilitation: results of the prospective, multicenter, randomized, single-blinded Everest trial," Neurorehabilitation and Neural Repair, 2016, vol. 30(2), pp. 107-119.
Li, Z. et al., "FE-Induced Muscular Torque Prediction with Evoked EMG Synthesized by NARX-Type Recurrent Neural Network," IEEE 2012, 6 pages.
Mestais, C. et al., "WIMAGINE: Wireless 64-channel ECoG recording implant for long term clinical applications," IEEE Transactions on Neural Systems and Rehabilitation Engineering, vol. 23, No. 1, Jan. 2015, 12 pages.
Miller, K. et al., "Reorganization of large-scale physiology in hand motor cortex following hemispheric stroke," Neurology 76, Mar. 8, 2011, 4 pages.
Mishra, J. et al., "Closed-Loop Rehabilitation of Age-Related Cognitive Disorders," Semin Neurol. Nov. 2014; 34(5), pp. 584-590.
Moritz, C. et al., "Direct control of paralysed muscles by cortical neurons," Nature, vol. 456, Dec. 4, 2008, 5 pages.
Mrachacz-Kersting, et al., "An Associative Brain-Computer-Interface for Acute Stroke Patients," The Scientific World Journal, vol. 2014, 11 pages.
Piangerelli, M. et al., "A fully integrated wireless system for intracranial direct cortical stimulation, real-time electrocorticography data transmission, and smart cage for wireless battery recharge," Frontiers in Neurology, Aug. 25, 2014, 5 pages.
Rao, R., "Brain-Computer Interfacing," Cambridge University Press, 2013, 15 pages.
Rao, R., "Method for augmenting the brain and nervous system with self-learning artificial networks for rewiring neural circuits and achieving desired functional outcomes," Feb. 26, 2018, 1 page.
Rao, R., Towards Neural Co-Processors for the Brain: Combining Decoding and Encoding in Brain-Computer Interfaces, Paul G. Allen School of Computer Science and Engineering, 14 pages.
Rebesco, J. et al., "Altering function in cortical networks by short-latency, paired stimulation," IEEE, 2010, 4 pages.

(56) References Cited

OTHER PUBLICATIONS

Rebesco, J. et al., "Rewiring neural interactions by microstimulation," Frontiers in Systems Neuroscience, Aug. 23, 2019, 15 pages.
Rouse, A.G. et al., "A chronic generalized bi-directional brain-machine interface," Journal of Neural Engineering 8 (2011), 20 pages.
Savic, A. et al.," Feasibility of a Hybrid Brain-Computer Interface for Advanced Functional Electrical Therapy," The Scientific World Journal, vol. 2014, 11 pages.
Sun, F. et al., "The RNS System: responsive cortical stimulation for the treatment of refractory partial epilepsy," Expert Reviews, pp. 1745-2422.
Sussillo, D. et al., "Generating coherent patterns of activity from chaotic neural networks," Neuron 63, Aug. 27, 2009, pp. 544-557.
Vansteensel, M. et al., "Fully implanted brain-computer interface in a locked-in patient with ALS," The New England Journal of Medicine, 375, Nov. 24, 2016, 7 pages.
Wright, J. et al., "A review of control strategies in closed-loop neuroprosthetic systems," Frontiers in Neuroscience, Jul. 12, 2016, 13 pages.
Non-Final Office Action dated Dec. 9, 2020 for U.S. Appl. No. 16/370,643, 7 pages.
Non-Final Office Action dated May 26, 2021 for U.S. Appl. No. 16/319,648, 20 pages.
Notice of Allowance dated May 20, 2021 for U.S. Appl. No. 16/370,643, 7 pages.
Final Office Action dated Jan. 12, 2022 for U.S. Appl. No. 16/319,648, 22 pages.

\* cited by examiner

SYSTEMS AND METHODS FOR BRAIN STIMULATION FOR RECOVERY FROM BRAIN INJURY, SUCH AS STROKE

CROSS-REFERENCE TO RELATED APPLICATION

The present application claims priority to U.S. Provisional Patent Application No. 62/660,035, filed Apr. 19, 2018, and titled "ACTIVITY-DEPENDENT HUMAN BRAIN SURFACE STIMULATION FOR RECOVERY FROM STROKE AND OTHER BRAIN INJURIES," which is incorporated herein by reference in its entirety.

STATEMENT REGARDING FEDERALLY SPONSORED RESEARCH

This invention was made with government support under Grant No. EEC-1028725, awarded by the National Science Foundation and Grant No. NIH-R01-NS-12542 awarded by the National Institutes of Health. The government has certain rights in the invention.

TECHNICAL FIELD

The present technology relates generally to restoring brain function. In particular, some embodiments of the present technology include systems and methods for promoting neuroplasticity in the brain of a subject to improve and/or restore neural function lost or diminished by injury.

BACKGROUND

Approximately 700,000 people in the United States suffer a stroke each year, and a large proportion of those people suffer motor or other deficits as a result. Current rehabilitation approaches lead to limited recovery of function, and there have been few developments of novel and effective pharmacological or surgical options for rehabilitation. Nevertheless, recent advances in neural technologies and our understanding of the human brain have sparked new investigations into the potential of brain-computer interfaces that directly record and/or stimulate the brain. For example, stimulation of the cerebral cortex has emerged as one possible tool for encouraging and facilitating recovery of function following focal cortical damage due to stroke or traumatic brain injury.

DETAILED DESCRIPTION

The present disclosure is directed generally toward systems and methods for promoting neuroplasticity in the nervous system (e.g., the brain or spinal cord) of a subject to improve and/or restore neural function. In several of the embodiments described below, a system for promoting neuroplasticity includes a first stimulating component configured to be implanted within and/or worn externally by the subject proximate to a first region of the brain. The first stimulating component is configured to receive a first stimulation pattern and to stimulate the first region of the brain based on the first stimulation pattern to promote neuroplasticity therein. In some embodiments, the first stimulating component is implanted proximate to the brain surface and configured to directly stimulate the brain surface. The system further includes a computing device communicatively coupled to the first stimulating component and configured to output the first stimulation pattern to the first stimulating component.

In some embodiments, in a movement-dependent and/or muscular-activity-dependent configuration, the system can further include one or more movement sensors (e.g., accelerometers) and/or one or more activity sensors (e.g., electromyography sensors) configured to detect movement or muscular activity, respectively, of the subject. For example, the sensors can detect the residual movement and/or muscular activity of a paretic limb. The computing device can be communicatively coupled to the movement sensors and/or the activity sensors and can generate and/or output the first stimulation pattern based on the detected movement and/or muscular activity of the subject.

In some embodiments, in a neural-activity-dependent configuration, the system can further include a neural sensor (e.g., including one or more electrocorticography electrodes) configured to detect and/or record neural signals at a second region of the brain. The computing device can be communicatively coupled to the neural sensor and can generate and/or output the first stimulation pattern based on the detected neural activity of the subject.

In some embodiments, in a paired-stimulation configuration, the system can include two stimulating components each configured to be implanted within and/or worn externally by the subject proximate to a relevant region of the brain. The two stimulating components are configured to sequentially stimulate the brain, typically with brief interstimulus intervals to promote neural plasticity. In some embodiments, this paired stimulation paradigm can be delivered in conjunction with the previously described activity-dependent stimulation.

It is expected that the systems and methods described herein can be used to promote neuroplasticity for the creation of new natural pathways between different areas of the brain (e.g., between the first and second regions, in the first region, in the second region, and/or in/between other regions directly or indirectly connected to these regions). These new neural pathways can function to replace lost neural function (e.g., resulting from injury) or to improve existing neural function in the brain or other parts of the nervous system.

Certain details are set forth in the following description and in FIGS. 1-7 to provide a thorough understanding of various embodiments of the present technology. In other instances, well-known structures, materials, operations and/or systems often associated with neural stimulation and recording (e.g., hardware and methods for stimulating the nervous system of a subject and/or recording neural signals from the nervous system such as electrical, optical, magnetic, chemical, and ultrasound-based recording and stimulation methods) are not shown or described in detail in the following disclosure to avoid unnecessarily obscuring the description of the various embodiments of the technology. Those of ordinary skill in the art will recognize, however, that the present technology can be practiced without one or more of the details set forth herein, or with other structures, methods, components, and so forth.

The terminology used below is to be interpreted in its broadest reasonable manner, even though it is presented in conjunction with a detailed description of certain examples of embodiments of the technology. Indeed, certain terms may even be emphasized below; however, any terminology intended to be interpreted in any restricted manner will be overtly and specifically defined as such in this Detailed Description section.

The accompanying Figures depict embodiments of the present technology and are not intended to be limiting of its scope. The sizes of various depicted elements are not necessarily drawn to scale, and these various elements may be arbitrarily enlarged to improve legibility. Component details may be abstracted in the Figures to exclude details such as position of components and certain precise connections between such components when such details are unnecessary for a complete understanding of how to make and use the invention.

Many of the details, dimensions, angles and other features shown in the Figures are merely illustrative of particular embodiments of the disclosure. Accordingly, other embodiments can have other details, dimensions, angles and features without departing from the spirit or scope of the present invention. In addition, those of ordinary skill in the art will appreciate that further embodiments of the invention can be practiced without several of the details described below.

In the Figures, identical reference numbers identify identical, or at least generally similar, elements. To facilitate the discussion of any particular element, the most significant digit or digits of any reference number refers to the Figure in which that element is first introduced. For example, element 110 is first introduced and discussed with reference to FIG. 1.

The following discussion provides a general description of a suitable environment in which the present technology may be implemented. Although not required, aspects of the technology are described in the general context of computer-executable instructions, such as routines executed by a general-purpose computer. Aspects of the technology can be embodied in a special purpose computer or data processor that is specifically programmed, configured, or constructed to perform one or more of the computer-executable instructions explained in detail herein. Aspects of the technology can also be practiced in distributed computing environments where tasks or modules are performed by remote processing devices, which are linked through a communication network (e.g., a wireless communication network, a wired communication network, a cellular communication network, the Internet, and/or a short-range radio network (e.g., via Bluetooth). In a distributed computing environment, program modules may be located in both local and remote memory storage devices.

Computer-implemented instructions, data structures, screen displays, and other data under aspects of the technology may be stored or distributed on computer-readable storage media, including magnetically or optically readable computer disks, as microcode on semiconductor memory, nanotechnology memory, organic or optical memory, or other portable and/or non-transitory data storage media. In some embodiments, aspects of the technology may be distributed over the Internet or over other networks (e.g. a Bluetooth network) on a propagated signal on a propagation medium (e.g., an electromagnetic wave(s) or a sound wave) over a period of time, or may be provided on any analog or digital network (e.g., packet switched, circuit switched, or other scheme).

Figure 1:
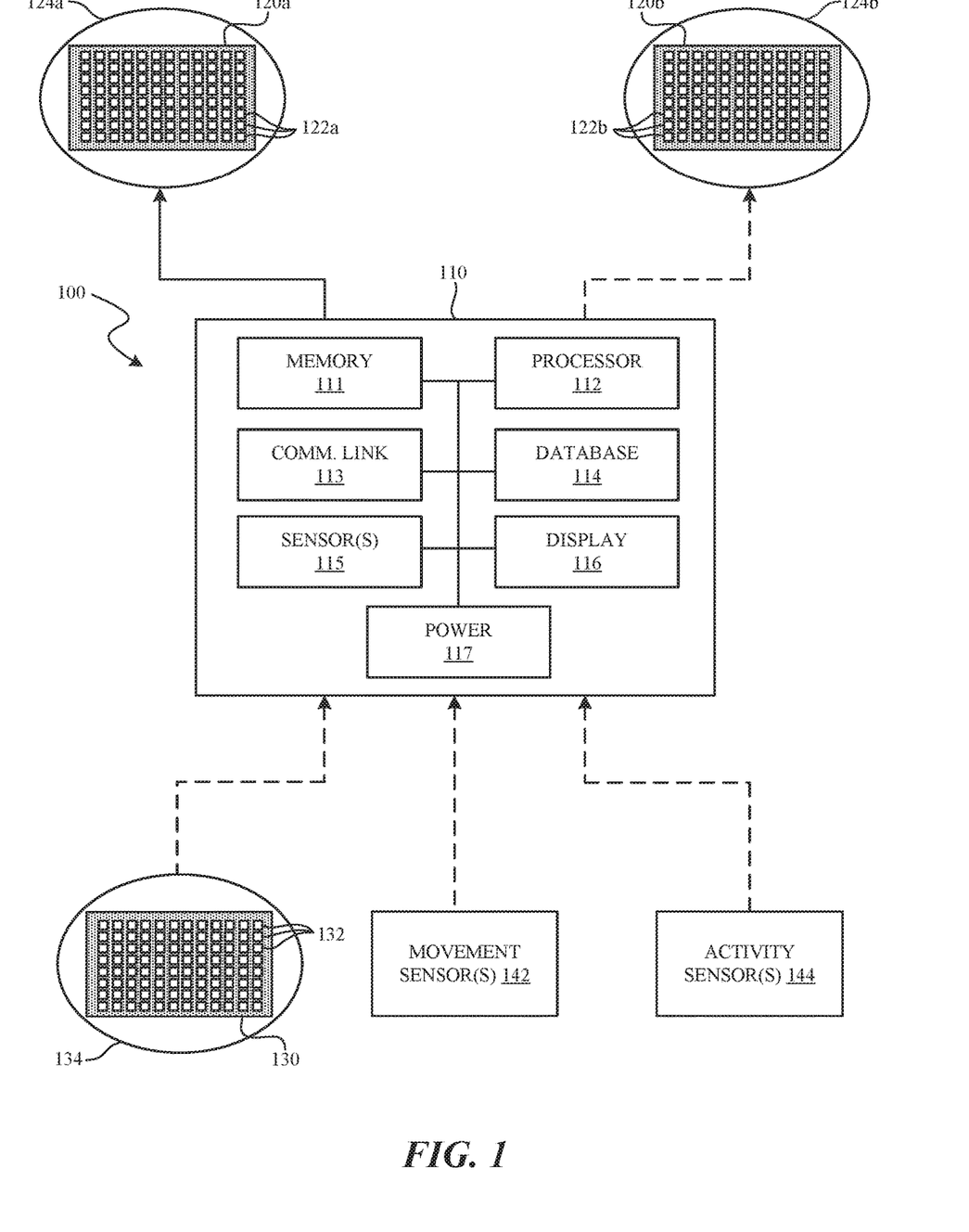
FIG. 1 is a partially schematic diagram of a system for promoting neuroplasticity in a subject to improve and/or restore neural function in accordance with an embodiment of the present technology.

FIG. 1 is a partially schematic diagram of a system 100 for promoting neuroplasticity in a subject (e.g., a human patient) to improve and/or restore neural function in accordance with an embodiment of the present technology. The system 100 includes a processing subsystem 110 configured to be communicatively/operably coupled to (a) one or more stimulation modules 120 including a first stimulation module 120a and optionally a second stimulation module 120b, (b) optionally a neural sensor module 130, (c) optionally one or more movement sensors 142, and (d) optionally one or more activity sensors 144. A simplified example of a suitable processing subsystem 110 is described in "*The Neurochip-2: An Autonomous Head-Fixed Computer for Recording and Stimulating in Freely Behaving Monkeys,*" by Stavros Zanos, Andrew G. Richardson, Larry Shupe, Frank P. Miles, and Eberhard E. Fetz, IEEE Transactions on Neural Systems And Rehabilitation Engineering, Vol. 19, No. 4, pg. 427-435, August 2011, which is also incorporated herein by reference in its entirety. An application of such a subsystem to induce neuroplasticity using a simple spike detection method is described in "*Long-term motor cortex plasticity induced by an electronic neural implant,*" by Andrew Jackson, Jaideep Mavoori, and Eberhard E. Fetz, Nature, Vol. 444, pg. 56-60, Nov. 2, 2006, which is also incorporated herein by reference in its entirety.

The first stimulation module 120a is configured to be positioned at or proximate to a first stimulation region 124a of the nervous system of the subject (e.g., the brain or spinal cord) of the subject (e.g., a first region in the primary motor cortex of the brain), and the second stimulation module 120b is configured to be positioned at or proximate to a second stimulation region 124b of the nervous system (e.g., a second region in the primary motor cortex of the brain). The stimulation modules 120 can be implanted in and/or worn externally by the subject, and can include any invasive or non-invasive hardware for stimulating the stimulation regions 124. For example, the stimulation modules 120 can be configured to stimulate the stimulation regions 124 using one or more of: electrical activation, optical activation, magnetic activation, ultrasonic activation, and chemical activation. In some embodiments, the stimulation modules 120 are multi-channel modules that each include a plurality of individual stimulating elements 122 (identified individually as first stimulating elements 122a and second stimulating elements 122b). Each of the stimulating elements 122 can be configured to stimulate the corresponding one of the stimulation regions 124 at a different location in and/or on the stimulation region, and to provide spatially and/or spatiotemporally differing stimulation patterns in and/or on the stimulation regions 124. In some embodiments, the number of individual stimulating elements 122 (e.g., stimulation channels) in the stimulation modules 120 can be selected to correspond to a characteristic (e.g., the physical structure) of the stimulation regions 124.

In a particular embodiment, the stimulation elements 122 can be electrocorticography (ECoG) electrodes that are configured to stimulate the surface of the brain of the subject. In such embodiments, the first stimulation module 120a can be implanted within the subject proximate to the brain surface, and the first stimulation region 124a can be a first region of the brain surface. Likewise, the second stimulation module 120b can be implanted within the subject proximate to the brain surface, and the second stimulation region 124b can be a second region of the brain surface.

The neural sensor module 130 is configured to detect neural signals (e.g., neuroelectrical activity, neurochemical activity, etc.) in the nervous system (e.g., the brain) of the subject. In some embodiments, the neural sensor module 130 is implanted in and/or worn externally proximate to a region of interest 134 of the brain of the subject. In some embodiments, the neural sensor module 130 can be a multi-channel sensor that includes a plurality of individual sensor elements 132 configured to detect one or more signals generated at different locations in and/or on the region of interest 134. For example, the sensor elements 132 can be configured to provide a spatial and/or spatiotemporal sampling of neural signals generated over the region of interest 134. More specifically, the sensor elements 132 can be configured to detect one or more of spikes, firing rates, local field potentials, optical or blood-oxygen level dependent (BOLD) activity, electroencephalogram (EEG) or electrocorticographic (ECoG) oscillatory features such as alpha waves, beta waves, gamma waves, etc., and the like. In a particular embodiment, the sensor elements 132 can be ECoG electrodes that are configured to record ECoG features (e.g., beta waves) at the brain surface. In some embodiments, the number of individual sensor elements 132 (e.g., measurement channels) in the neural sensor module 130 can be selected to correspond to a characteristic of the region of interest 134 (e.g., the physical structure of the region, the degrees of freedom in a detectable signal at the region, the numbers of neurons in the region, etc.).

The movement sensors 142 are configured to detect and/or record one or more movements of the subject. For example, the movement sensors 142 can be positioned on (e.g., attached to) a limb (e.g., a hand, leg, or arm) of the subject. The movement sensors 142 can include inertial measurement units (IMUs) having accelerometers, gyroscopes, and/or other components for detecting movement of the limb. In other embodiments, the movement sensors 142 can include cameras, RFID readers, or other devices for recording movement of the subject without being directly attached to the subject.

The activity sensors 144 are configured to detect and/or record muscular activity (e.g., skeletal-muscular activity) of the subject. For example, the activity sensors 144 can be implanted within a limb of the subject and/or positioned on the surface of the skin of the limb for recording electromyography (EMG) signals generated in one or more muscles in the limb.

As described in greater detail below with reference to FIGS. 2 and 3, in some embodiments the system 100 can include only the first stimulation module 120a, and the movement sensors 142 and/or the activity sensors 144, for implementing a method of closed-loop stimulation for promoting neuroplasticity and improving neural control of limb movement based on detected residual movement or muscle activity of the (e.g., paretic) limb. As described in greater detail below with reference to FIGS. 4 and 5, in other embodiments the system 100 can include only the first stimulation module 120a and the neural sensor module 130 for implementing a method of closed-loop stimulation for promoting neuroplasticity based on detected neural signals. As described in greater detail below with reference to FIGS. 6 and 7, in yet other embodiments the system 100 can include only the first stimulation module 120a and the second stimulation module 120b for implementing a method of paired-pulse stimulation for promoting neuroplasticity.

The processing subsystem 110 comprises several components including memory 111 (e.g., one or more computer readable storage modules, components, devices, etc.) and one or more processors 112. The memory 111 can be configured to store information (e.g., signal data, subject information or profiles, environmental data, data collected from one or more sensors, media files, etc.) and/or executable instructions that can be executed by the one or more processors 112. The memory 111 can include, for example, instructions for (a) processing data from the neural sensor module 130, the movement sensors 142, and/or the activity sensors 144 and/or (b) generating stimulation patterns for output to the stimulation modules 120. The processing subsystem 110 also includes a communication link 113 (e.g., a wired communication link and/or a wireless communication link (e.g., Bluetooth, Wi-Fi, infrared, and/or another wireless radio transmission network)) and a database 114 configured to store data (e.g., signal data acquired from a region of interest, equations, filters, etc.) used in the techniques for promoting plasticity and/or enhancing neural activity, connectivity, and/or outflow for restoring neural function, as disclosed herein.

One or more sensors 115 can provide additional data for use in restoring function in the subject. The sensors 115 can also provide other data pertinent to a condition and/or environment of the subject. For example, the sensors 115 may include one or more ECoG or other neural sensors, voltammetry sensors of neurochemicals, blood pressure monitors, galvanometers, accelerometers, thermometers, hygrometers, blood pressure sensors, altimeters, gyroscopes, magnetometers, proximity sensors, barometers, microphones, cameras, Global Positioning System (GPS) sensors, Near Field Communication (NFC) sensors, etc. The sensors 115 can also be configured to provide information about the system 100 itself, such as an operating condition (e.g., power level, noise level, etc.) of any or all of the components included therein. One or more displays 116 can provide video output and/or graphical representations of data obtained by the system 100. The one or more displays 116 and/or other components of the processing subsystem 110 can include one or more input devices (e.g., buttons, touchscreens, keyboards, mice, joysticks, number pads, etc.) for receiving user input. A power supply 117 (e.g., a power cable, one or more batteries, and/or one or more capacitors) can provide electrical power to components of the processing subsystem 110 and/or the system 100. In embodiments that include one or more batteries (e.g., where the system 100 is a portable system), the power supply 117 can be configured to recharge, for example, via a power cable, inductive charging, and/or another suitable recharging method.

In some embodiments, the processing subsystem 110 can include one or more components partially or wholly incorporated into the stimulation modules 120, the neural sensor module 130, the movement sensors 142, and/or the activity sensors 144. In other embodiments, however, the processing subsystem 110 may include components remote from the stimulation modules 120, the neural sensor module 130, the movement sensors 142, and/or the activity sensors 144, and connected thereto by a communication network (e.g., the Internet and/or another network or cloud computers). In some embodiments, for example, at least a portion of the processing subsystem 110 may reside on a mobile device (e.g., a mobile phone, a tablet, a personal digital assistant, etc.) and/or a computer (e.g., a desktop computer, a laptop, etc.) communicatively coupled to the stimulation modules 120, the neural sensor module 130, the movement sensors 142, and/or the activity sensors 144. Moreover, the processing subsystem 110 can be configured to be worn by the subject (e.g., carried by their body) and/or implanted in their body (e.g., in or on a region of their nervous system). More generally, the system 100 can be made sufficiently small to be worn externally and/or implanted in the subject and operate autonomously during hours of free and/or controlled behavior.

Figure 2:
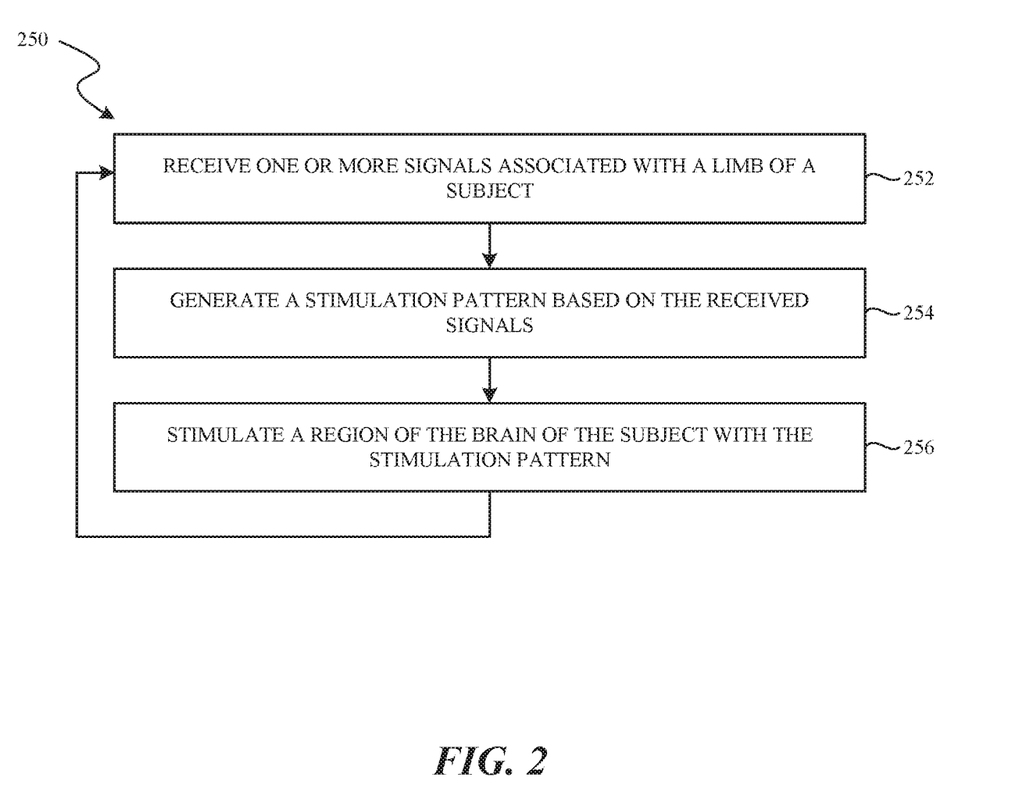
FIG. 2 is a flow diagram of a process or method for promoting neuroplasticity in a subject based on detected limb movement or muscular activity to improve and/or restore neural function in accordance with an embodiment of the present technology.

FIG. 2 is a flow diagram of a process or method 250 for promoting neuroplasticity in a subject (e.g., a human patient) based on detected limb movement or muscular activity to improve and/or restore neural function in accordance with an embodiment of the present technology. In particular, the method 250 can operate to improve neural control of the movement of a limb, such as a paretic limb with reduced function as a result of a stroke, traumatic brain injury, disease, etc. The method 250 can include instructions stored, for example, in the memory 111 of the system 100 (FIG. 1) that are executable by the one or more processors 112 (FIG. 1). In some embodiments, portions of the method 250 are performed by one or more hardware components of the system 100 (e.g., the first stimulation module 120*a* and the movement sensors 142 and/or the activity sensors 144 of FIG. 1). FIG. 3, for example, is a schematic view of the system 100 of FIG. 1 in a movement-dependent and/or activity-dependent configuration for promoting neuroplasticity in, for example, a brain 360 of a subject in accordance with an embodiment of the present technology. For the sake of illustration, some features of the method 250 will be described in the context of the embodiment shown in FIG. 3.

Beginning at block 252, the method 250 includes receiving one or more signals associated with a limb of a subject. For example, in the embodiment illustrated in FIG. 3, the processing subsystem 110 can receive one or more movement signals $m_1$-$m_n$ from the movement sensor(s) 142 and/or one or more activity signals $a_1$-$a_o$ from the activity sensor(s) 144. In some embodiments, the system 100 includes only the movement sensors 142 or the activity sensors 144, and therefore the processing subsystem 110 receives only the movement signals $m_1$-$m_n$ or the activity signals $a_1$-$a_o$. The movement signals $m_1$-$m_n$ are representative of detected movements of the limb of the subject (e.g., electric signals representative of accelerations, velocities, spatial positions, etc., of the limb). The activity signals $a_1$-$a_o$ are representative of detected activity of one or more muscles within the limb (e.g., EMG signals).

At block 254, the method 250 includes generating a stimulation pattern based on the received signals associated with the limb of the subject. For example, as shown in FIG. 3 the processing subsystem 110 can generate a stimulation pattern comprising a plurality of stimulation signals $s_1$-$s_m$. The memory 111 (FIG. 1) of the processing subsystem 110 can store instructions executable by the one or more processors 112 (FIG. 1) for mapping/transforming the movement signals $m_1$-$m_n$ and/or the activity signals $a_1$-$a_o$ (e.g., the inputs) to the stimulation signals $s_1$-$s_m$ (e.g., the outputs). In some embodiments, the movement signals $m_1$-$m_n$ and/or the activity signals $a_1$-$a_o$ are directly mapped to the stimulation signals $s_1$-$s_m$ such that there is a one-to-one correspondence between the signals (e.g., n=o=m, o=m, n=m, n+o=m, etc.). In one aspect of the present technology, such a mapping requires the processing subsystem 110 to perform only relatively simple processing. For example, the processing subsystem 110 can map the movement signals $m_1$-$m_n$ and/or the activity signals $a_1$-$a_o$ to the stimulation signals $s_1$-$s_m$ using a suitable look-up table stored in the memory 111. In other embodiments, the mapping of the movement signals $m_1$-$m_n$ and/or the activity signals $a_1$-$a_o$ to the stimulation signals $s_1$-$s_m$ can be any suitable mapping (e.g., n≠m, o≠m, n≠m≠o, etc.), and/or can be based on more complicated processing. For example, the processing subsystem 110 can be configured to map the movement signals $m_1$-$m_n$ and/or the activity signals $a_1$-$a_o$ to the stimulation signals $s_1$-$s_m$ using a neural model (e.g., a neural or artificial network), parametric regression, nonparametric regression, and/or other suitable method.

At block 256, the method 250 includes stimulating a region of the brain of the subject with the stimulation pattern. For example, in the embodiment illustrated in FIG. 3, the stimulation pattern is output to the first stimulation region 124*a* via the first stimulation module 120*a*. The first stimulation region 124*a* can be a region of the brain 360 implicated in controlling movement of the limb, such as a region of the motor cortex. In some embodiments, the first stimulation region 124*a* can be an injured region that was previously injured by stroke, traumatic brain injury, or disease. In other embodiments, the first stimulation region 124*a* can be another region of the nervous system of the subject, such as a region of the spinal cord. The stimulation signals $s_1$-$s_m$ are each configured to stimulate a different portion of the first stimulation region 124*a* (e.g., via the individual stimulating elements 122*a*). In some embodiments, the stimulation signals $s_1$-$s_m$ are operable to stimulate the first stimulation region 124*a* simultaneously or nearly simultaneously, while in other embodiments the stimulation signals $s_1$-$s_m$ are operable to stimulate the first stimulation region 124*a* over a varying time period (e.g., via a pulsed delivery). The number of output stimulation signals $s_1$-$s_m$ can depend on the specific anatomy of the first stimulation region 124*a* as well as the configuration of the first stimulation module 120*a* (e.g., the number of first stimulating elements 122*a*.) The output stimulation signals $s_1$-$s_m$ can include electrical signals, optical signals, magnetic signals, ultrasonic signals, voltammetric signals, and/or other suitable signals.

Lastly, the method 250 returns to block 252 and the method 250 can be repeated. In one aspect of the present technology, the system 100 is a closed-loop system that generates and outputs a new stimulation pattern each time that movement or activity of the limb is detected (e.g., via receipt of the movement signals $m_1$-$m_n$ and/or the activity signals $a_1$-$a_o$). More generally, the system 100 is configured such that movement/activity of the limb triggers stimulation of a region of the brain 360 associated with (e.g., implicated in) that movement. In some embodiments, the system 100 can operate while the subject receives physical and/or occupational therapy that encourages movement of the limb.

In another aspect of the present technology, outputting the stimulation pattern to the first stimulation region 124*a* of the brain 360 promotes neuroplasticity—e.g., increases and/or enhances the activity and connectivity of neural circuits controlling movements—in the first stimulation region 124a and/or elsewhere in the brain 360 (e.g., in and/or between other regions directly or indirectly connected to the first stimulation region 124a). That is, the method 250 can promote neuroplasticity, rewiring, and creation of new neural pathways between populations of neurons for restoration and rehabilitation of function, such as enabling controlled movement of a previously paretic limb.

Figure 4:
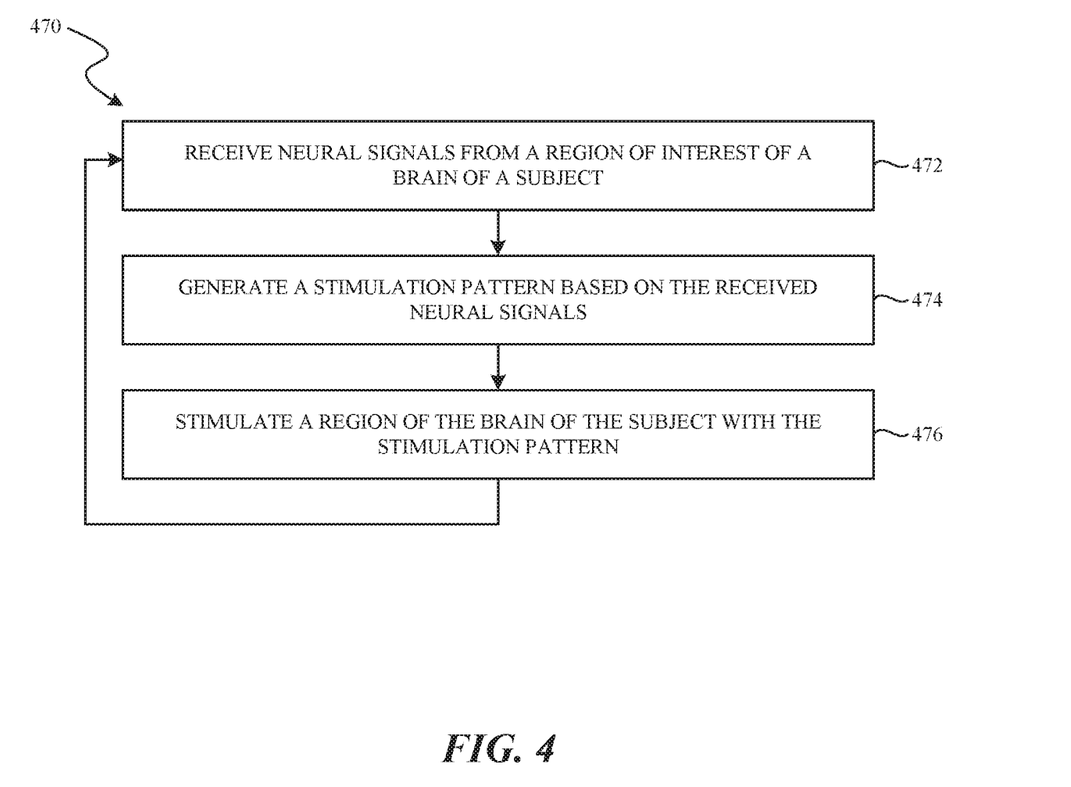
FIG. 4 is a flow diagram of a process or method for promoting neuroplasticity in a subject based on detected neural activity to improve and/or restore neural function in accordance with an embodiment of the present technology.
Figure 5:
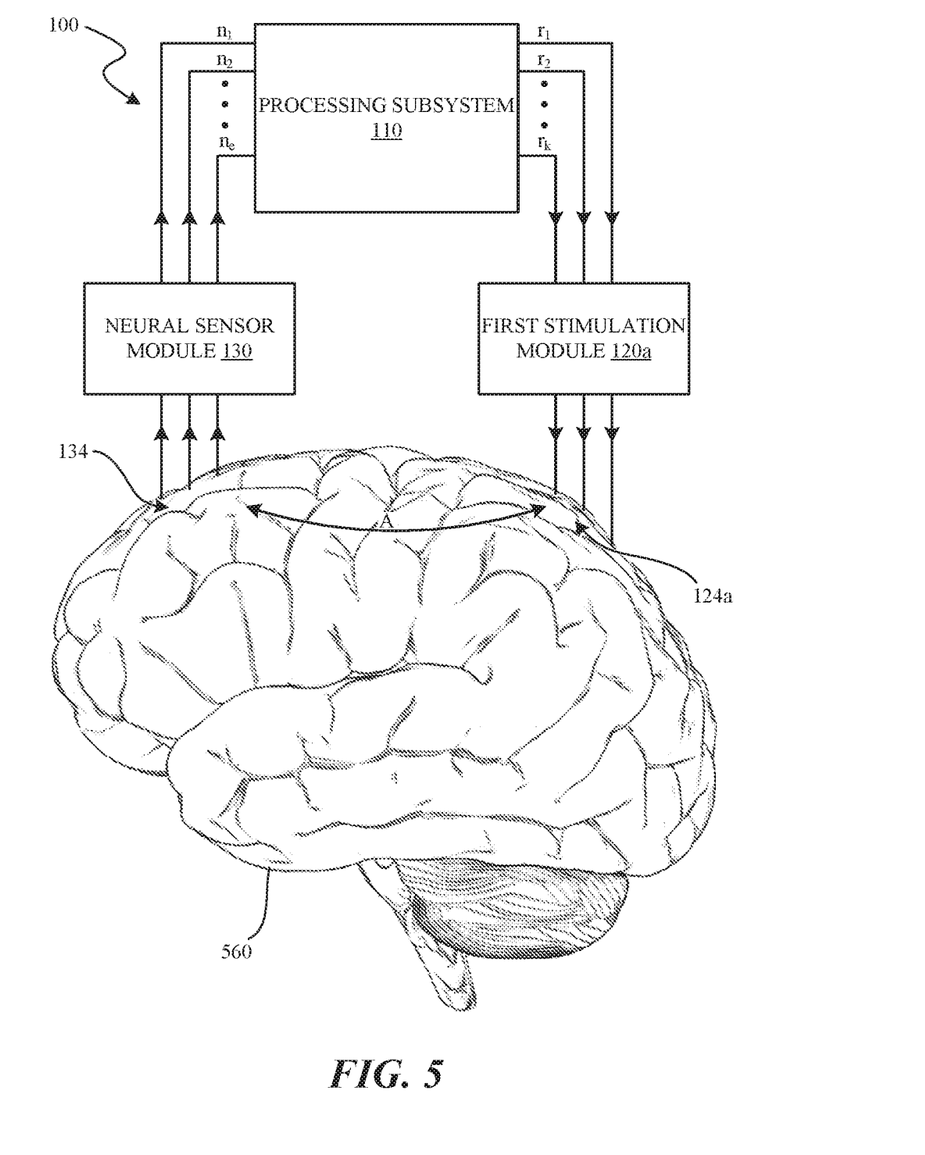
FIG. 5 is a schematic diagram of the system of FIG. 1 in a neural-activity-dependent configuration in accordance with embodiments of the present technology.

FIG. 4 is a flow diagram of a process or method 470 for promoting neuroplasticity in a subject (e.g., a human patient) based on detected neural activity to improve and/or restore neural function in accordance with an embodiment of the present technology. In particular, the method 470 can operate to promote neuroplasticity by delivering stimulation based on the detected neural activity. Similar to the method 250 described in detail above, the method 470 can include instructions stored in the memory 111 of the system 100 (FIG. 1) that are executable by the one or more processors 112 (FIG. 1). In some embodiments, portions of the method 470 are performed by one or more hardware components of the system 100 (e.g., the first stimulation module 120a and the neural sensor module 130 of FIG. 1). FIG. 5, for example, is a schematic view of the system 100 of FIG. 1 in a neural-activity-dependent configuration for promoting neuroplasticity in, for example, a brain 560 of a subject in accordance with an embodiment of the present technology. For the sake of illustration, some features of the method 470 will be described in the context of the embodiment shown in FIG. 5.

Beginning at block 472, the method 470 includes receiving neural signals from a region of interest of the brain of the subject. For example, in the embodiment illustrated in FIG. 5, the processing subsystem 110 receives a plurality of neural signals $n_1$-$n_e$ via the neural sensor module 130 from the region of interest 134, which is a region of the brain 560 of the subject. The neural signals $n_1$-$n_e$ are representative of neuroelectrical and/or neurochemical activity in the brain 560. In some embodiments, each of the neural signals $n_1$-$n_e$ is detected at and/or recorded from a different spatial location of the region of interest 134, and/or at one or more different times. In certain embodiments, the neural signals $n_1$-$n_e$ are ECoG recordings of neural oscillations (e.g., brainwaves) having a frequency range of, for example, between about 15-25 Hz (e.g., beta waves) or between about 25-100 Hz (e.g., gamma waves). In some embodiments, the neural signals $n_1$-$n_e$ are recorded while the subject performs a particular task. For example, if the goal of the method 470 is to restore a motor function of the subject, the neural signals $n_1$-$n_e$ may be recorded while the subject performs or attempts to perform the specific motor function to be restored (e.g., during physical and/or occupational therapy).

At block 474, the method 470 includes generating a stimulation pattern based on the received neural signals. For example, as shown in FIG. 5 the processing subsystem 110 can generate a stimulation pattern comprising a plurality of stimulation signals $r_1$-$r_k$. The memory 111 (FIG. 1) of the processing subsystem 110 can store instructions executable by the one or more processors 112 (FIG. 1) for mapping/transforming the neural signals $n_1$-$n_e$ (e.g., the inputs) to the stimulation signals $r_1$-$r_k$ (e.g., the outputs). In some embodiments, the neural signals $n_1$-$n_e$ are directly mapped to the stimulation signals $r_1$-$r_k$ such that there is a one-to-one correspondence between the signals (e.g., e=k). In other embodiments, the mapping of the neural signals $n_1$-$n_e$ to the stimulation signals $r_1$-$r_k$ can be any suitable mapping (e.g., e≠k).

At block 476, the method 470 includes stimulating a region of the brain of the subject with the stimulation pattern. For example, in the embodiment illustrated in FIG. 5, the stimulation pattern is output to the first stimulation region 124a via the first stimulation module 120a. The stimulation of the first stimulation region 124a with the stimulation signals $r_1$-$r_k$ can operate generally identically or similarly to that described in detail above with reference to block 256 of FIG. 2. For example, the stimulation signals $r_1$-$r_k$ can each stimulate a different portion of the first stimulation region 124a, and can be delivered simultaneously, nearly simultaneously, or over a varying time period (e.g., via a pulsed delivery). Likewise, the number stimulation signals $r_1$-$r_k$ can depend on the specific anatomy of the first stimulation region 124a as well as the configuration of the first stimulation module 120a, and the stimulation signals $r_1$-$r_k$ can include electrical signals, optical signals, magnetic signals, ultrasonic signals, voltammetric signals, and/or other suitable signals.

In some embodiments, the first stimulation region 124a is a different region than the region of interest 134. For example, the first stimulation region 124a and the region of interest 134 can be regions of the brain 560 that are separated by an injured region. The injured region could be caused by stroke, traumatic brain injury, disease, etc., and can partially or fully disconnect the region of interest 134 from the first stimulation region 124a. The system 100 can therefore "bridge" or "straddle" an injured region of the brain 560. In other embodiments, the first stimulation region 124a can be another region of the nervous system of the subject, such as a region of the spinal cord. For example, the injured region could be the result of a spinal cord injury, in which case the region of interest 134 can be a motor intention-forming region of the brain and the first stimulation region 124a can be a region of the spinal cord below the injury. By stimulating the first stimulation region 124a based on the neural signals $n_1$-$n_e$ detected in the region of interest 134, the system 100 can induce new neural connections (a) between the region of interest 134 and the first stimulation region 124a (represented by arrow A in FIG. 5), (b) in the first stimulation region 124a, (c) in the region of interest 134, and/or (d) in and/or between other regions directly or indirectly connected to these regions. The new neural connections may increase plasticity through and/or around the injured region to restore function that was previously lost as a result of the injury.

Lastly, the method 470 returns to block 472 and the method 470 can be repeated. In one aspect of the present technology, the system 100 is a closed-loop system that generates and outputs a new stimulation pattern each time that specified neural activity is detected (e.g., upon detection of the neural signals $n_1$-$n_1$). More generally, the system 100 can be configured such that particular neural activity, such as neural activity associated with a function to be restored, triggers stimulation of the brain 560.

Figure 6:
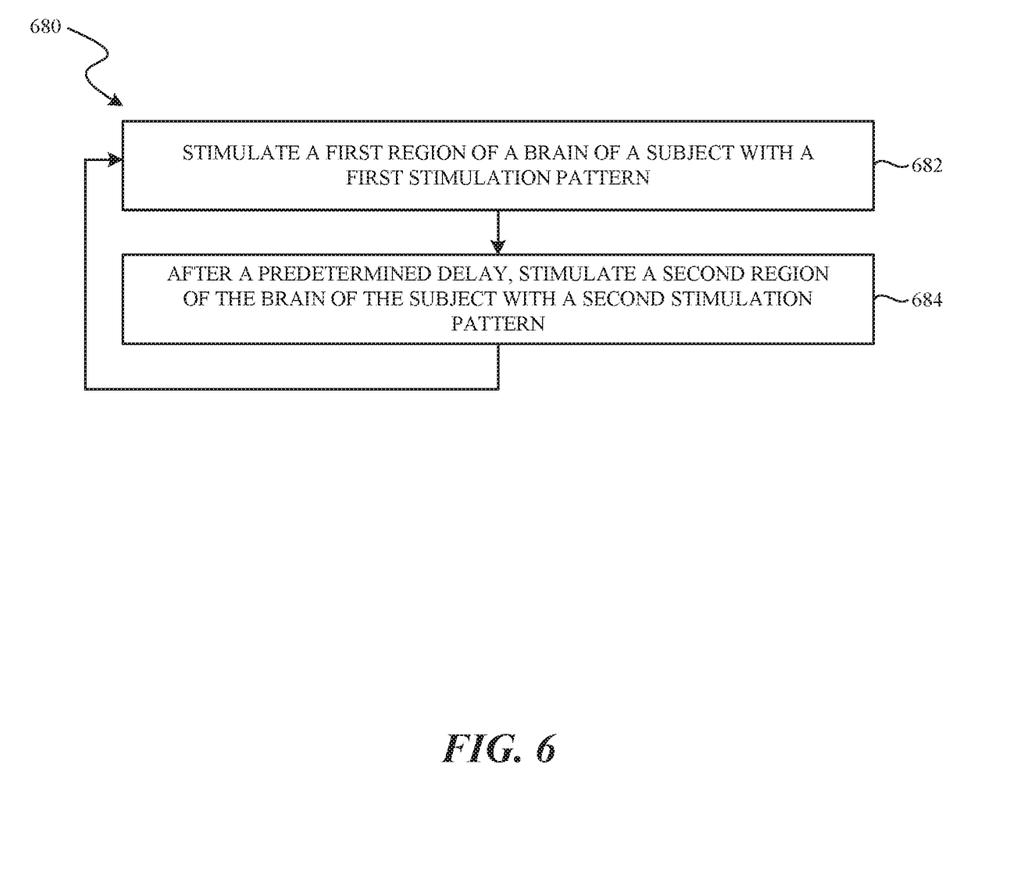
FIG. 6 is a flow diagram of a process or method for promoting neuroplasticity in a subject via paired-stimulation to improve and/or restore neural function in accordance with an embodiment of the present technology.
Figure 7:
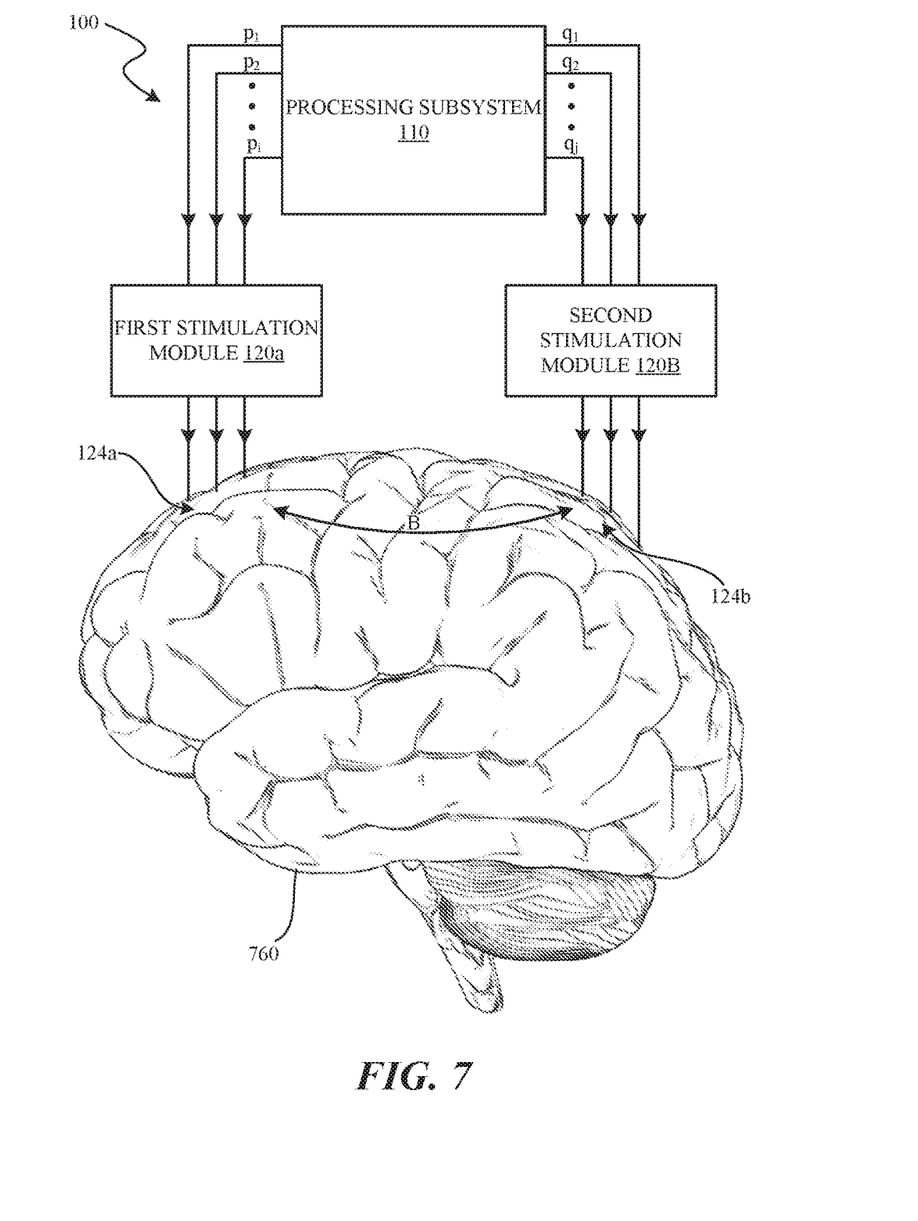
FIG. 7 is a schematic diagram of the system of FIG. 1 in a paired-stimulation configuration in accordance with an embodiment of the present technology.

FIG. 6 is a flow diagram of a process or method 680 for promoting neuroplasticity in a subject (e.g., a human patient) via paired-stimulation to improve and/or restore neural function in accordance with another embodiment of the present technology. Similar to the methods 250 and 470 described in detail above, the method 680 can include instructions stored in the memory 111 of the system 100 (FIG. 1) that are executable by the one or more processors 112 (FIG. 1). In some embodiments, portions of the method 680 are performed by one or more hardware components of the system 100 (e.g., the first stimulation module 120a and the second stimulation module 120b of FIG. 1). FIG. 7, for example, is a schematic view of the system 100 of FIG. 1 in a paired-stimulation configuration for promoting neuroplasticity in, for example, a brain 760 of a subject in accordance with an embodiment of the present technology. For the sake of illustration, some features of the method 680 will be described in the context of the embodiment shown in FIG. 7.

Beginning at block 682, the method 680 includes stimulating a first region of the brain of the subject with a first stimulation pattern. For example, in the embodiment illustrated in FIG. 7, the first stimulation pattern comprises a plurality of first stimulation signals $p_1$-$p_i$ that are output to the first stimulation region 124a, which is a region of the brain 760, via the first stimulation module 120a. At block 684, the method 680 includes stimulating a second region of the brain of the subject with a second stimulation pattern a predetermined time after stimulating the first region with the first stimulation pattern. For example, as shown in FIG. 7, the second stimulation pattern comprises a plurality of second stimulation signals $q_1$-$q_j$ that are output to the second stimulation region 124b, which is another region of the brain 760, via the second stimulation module 120b. Lastly, the method 680 returns to block 682 and the method 680 can be repeated. In other embodiments, the first stimulation region 124a and/or the second stimulation region 124b can be another region of the nervous system of the subject, such as a region of the spinal cord.

Put differently, the method 680 includes delivering the first stimulation signals $p_1$-$p_i$ to the first stimulation region 124a at one or more first times and then delivering the second stimulation signals $q_1$-$q_j$ to the second stimulation region 124b at one or more second times, different than the first times. In some embodiments, the time delay(s) between delivery of the first stimulation signals $p_1$-$p_i$ and delivery of the second stimulation signals $q_1$-$q_j$ is between about 5-25 milliseconds. Delivering the second stimulation signals $q_1$-$q_j$ at appropriate times after the first stimulation signals $p_1$-$p_i$ can induce neuroplasticity between (a) the stimulation regions 124 (represented by arrow B in FIG. 7), (b) in the first stimulation region 124a, (c) in the second stimulation region 124b, and/or (d) in and/or between other regions directly or indirectly connected to these regions. In the embodiment illustrated in FIG. 7, the stimulation regions 124 are different regions of the brain 760 that can, for example, bridge, straddle, or otherwise be functionally associated with an injured region of the brain 760. Therefore, the method 680 can operate to induce new neural connections and increase plasticity through and/or around the injured region to restore function that was previously lost as a result of the injury.

In general, the first and second stimulation patterns are known a priori. However, in some embodiments the first stimulation pattern and/or the second stimulation pattern can be fined-tuned before, after, or during operation of the system 100. For example, the method 680 can include adjusting one or more amplitudes of the stimulation patterns, adjusting one or more delivery delay times, etc. The stimulation of the stimulation regions 124 can operate generally identically or similarly to that described in detail above with reference to blocks 256 and 456 of FIGS. 2 and 4, respectively. For example, the first stimulation signals $p_1$-$p_i$ can each stimulate a different portion of the first stimulation region 124a, and can be delivered simultaneously, nearly simultaneously, or over a varying time period (e.g., via a pulsed delivery), and the second stimulation signals $q_1$-$q_j$ can each stimulate a different portion of the second stimulation region 124b, and can be delivered simultaneously, nearly simultaneously, or over a varying time period (e.g., via a pulsed delivery). The number of the first stimulation signals $p_1$-$p_i$ can be the same or different as the number of the second stimulation signals $q_1$-$q_j$ (e.g., i=j or i≠j) and the number of signals can depend on the specific anatomy of the stimulation regions 124 as well as the configuration of the stimulation modules 120. The first stimulation signals $p_1$-$p_i$ and the second stimulation signals $q_1$-$q_j$ can include electrical signals, optical signals, magnetic signals, ultrasonic signals, voltammetric signals, and/or other suitable signals.

Figure 3:
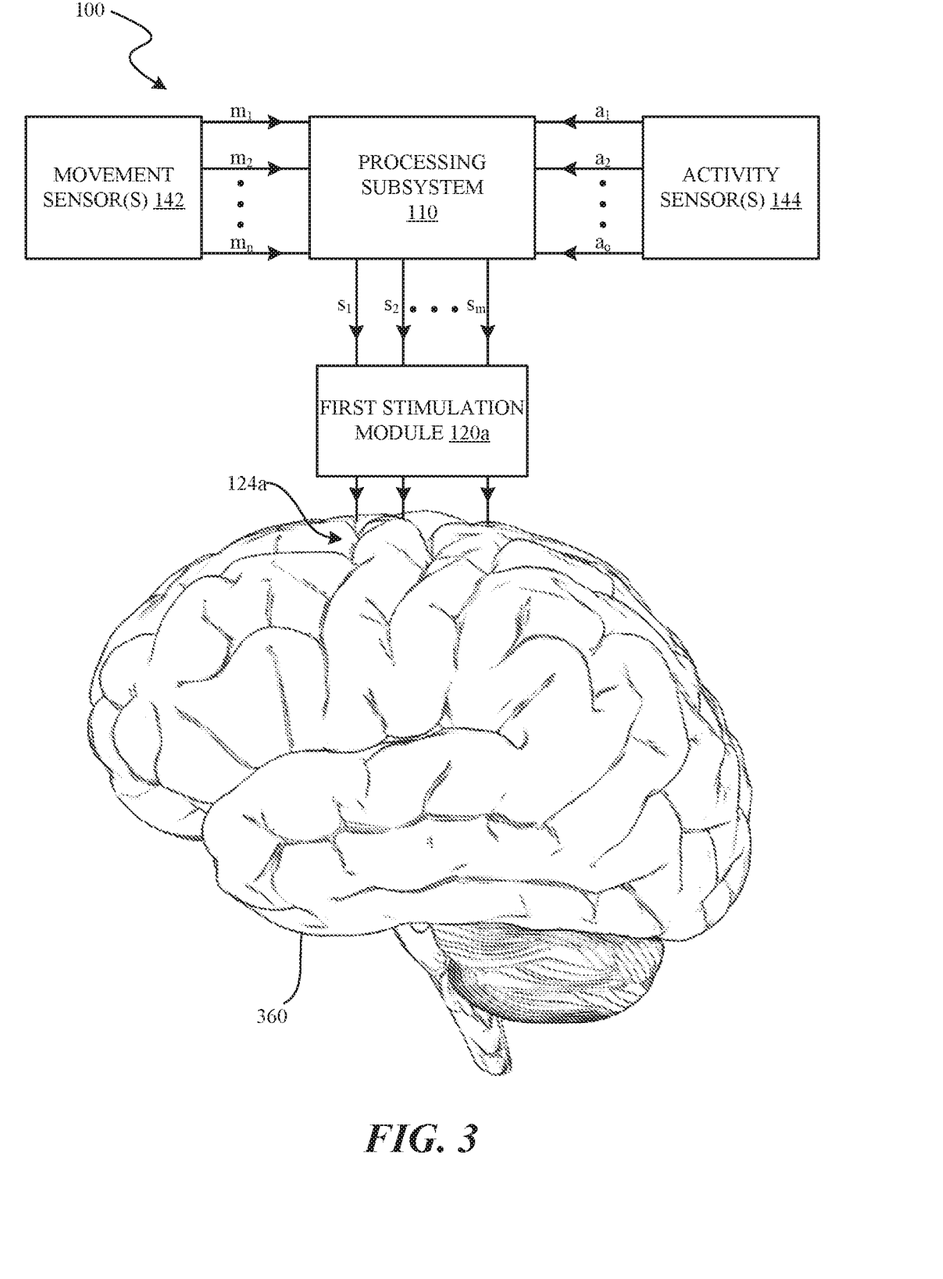
FIG. 3 is a schematic diagram of the system of FIG. 1 in a movement-dependent and/or muscular-activity-dependent configuration in accordance with an embodiment of the present technology.

Referring to FIGS. 1-7 together, in other embodiments the system 100 can be configured with different combinations of the stimulation modules 120, neural sensor module 130, movement sensors 142, and/or activity sensors 144, and/or the various blocks of the methods 250, 470, and 680 can be combined and/or executed in a different order. For example, the system 100 can be configured for both paired-pulse stimulation (FIGS. 6 and 7) and for detecting movement and/or activity of a paretic limb (FIGS. 2 and 3). In some such embodiments, movement of the paretic limb as detected by the movement sensors 142 and and/or activity sensors 144 can be used to pace the delivery of paired-stimulation by the stimulation modules 120. For example, detected limb movement can trigger the delivery of a first stimulation pattern in a paired sequence. That is, the signals from the movement sensors 142 and/or the activity sensors 144 can operate as trigger signals that trigger delivery of the first stimulation pattern when received by the processing subsystem 110. The subsequent delivery of a second, paired stimulation pattern can then be based on the timing of the delivery of the first stimulation pattern or, alternatively, also on the detected limb movement. Similarly, detected neural activity (FIGS. 4 and 5) could be used to pace the delivery of paired-stimulation from the stimulation modules 120. As one of ordinary skill in the art will appreciate, many such combinations are possible and are within the scope of the present technology.

Over time, dependence on the system 100 may be gradually reduced and the system 100 may be removed if sufficient function has been restored by the neuroplasticity induced by the use of system 100 over an extended period of time. In some embodiments, the system 100 may be configured as a permanent neural prosthesis.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. Moreover, the various embodiments described herein may also be combined to provide further embodiments (e.g., the disclosed system may include components for simultaneous augmentation and restoration of function in a nervous system of a subject).

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms may also include the plural or singular term, respectively. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A closed-loop system for promoting neuroplasticity in a brain of a subject to improve and/or restore neural control of a limb of the subject, the closed-loop system comprising:
    a sensor configured to be worn externally on the limb of the subject, wherein the sensor is configured to detect one or more signals associated with the limb of the subject;
    a stimulating component configured to be implanted within and/or worn externally by the subject proximate to a region of the brain implicated in controlling movement of the limb, wherein the stimulating component is configured to receive a stimulation pattern and to stimulate the region of the brain based on the stimulation pattern; and
    a computing device communicatively coupled to the sensor and the stimulating component, the computing device having a memory containing non-transitory computer-executable instructions and a processor for executing the non-transitory computer-executable instructions contained in the memory, wherein the non-transitory computer-executable instructions include instructions for:
        receiving the signals associated with the limb of the subject from the sensor;
        generating the stimulation pattern based on the received signals associated with the limb of the subject; and
        outputting the stimulation pattern to the stimulating component to promote neuroplasticity in the region of the brain by increasing or enhancing activity of neural circuits controlling movement of the limb,
        wherein the computing device is configured to generate a new stimulation pattern each time the computing device receives the detected one or more signals associated with a specified activity of the limb and output the new stimulation pattern to the stimulating component in a closed-loop manner.

2. The closed-loop system of claim 1 wherein the sensor is configured to detect movement of the limb, and wherein the signals associated with the limb of the subject are signals representative of the movement of the limb.

3. The closed-loop system of claim 2 wherein the sensor is an inertial measurement unit configured to be worn externally on the limb of the subject.

4. The closed-loop system of claim 1 wherein the sensor is configured to detect electrical activity of a muscle in the limb, and wherein the signals associated with the limb of the subject are signals representative of the electrical activity of the muscle.

5. The closed-loop system of claim 1 wherein the signals associated with the limb of the subject are electromyography signals.

6. The closed-loop system of claim 1 wherein the sensor is a movement sensor configured to detect movement of the limb, wherein the signals associated with the limb of the subject are signals representative of the movement of the limb, and wherein the closed-loop system further comprises:
    an activity sensor configured to be implanted within and/or worn externally on the limb of the subject and configured to detect electrical activity of a muscle in the limb, wherein the non-transitory computer-executable instructions further include instructions for:
        receiving (a) the signals representative of the movement of the limb from the movement sensor and (b) the detected electrical activity of the muscle from the activity sensor; and
    generating the stimulation pattern based on (a) the signals representative of the movement of the limb and (b) the detected electrical activity of the muscle.

7. The system of claim 1 wherein the stimulating component is configured to be worn proximate to the surface of the brain of the subject, and wherein the region is a region of the surface of the brain.

8. The system of claim 1 wherein the computing device is configured to be implanted in and/or worn by the subject.

9. The closed-loop system of claim 1 wherein:
    promoting the neuroplasticity in the region of the brain implicated in controlling movement of the limb by the closed-loop system is gradually reduced; and
    the closed-loop system including the externally worn stimulating component is configured to be removed from the subject when sufficient function of the limb has been restored.

10. A closed-loop system for promoting neuroplasticity in a brain of a subject to improve and/or restore neural function, the closed-loop system comprising:
    a sensor configured to detect one or more signals associated with a limb of the subject;
    a first stimulating component configured to be worn externally by the subject proximate to a first region of the brain implicated in controlling movement of the limb, wherein the first stimulating component is configured to receive a first stimulation pattern and to stimulate the first region of the brain based on the first stimulation pattern;
    a second stimulating component configured to be worn externally by the subject proximate to a second region of the brain, wherein the second stimulating component is configured to receive a second stimulation pattern and to stimulate the second region of the brain based on the second stimulation pattern; and
    a computing device communicatively coupled to the first and second stimulating components, the computing device having a memory containing non-transitory computer-executable instructions and a processor for executing the non-transitory computer-executable instructions contained in the memory, wherein the non-transitory computer-executable instructions include instructions for;
        outputting the first stimulation pattern to the first stimulating component responsive to the one or more signals; and
        a predetermined time after outputting the first stimulation pattern, outputting the second stimulation pattern to the second stimulating component, wherein outputting the first stimulation pattern and the second stimulation pattern is to promote neuroplasticity in the region of the brain by increasing or enhancing activity of neural circuits controlling movement of the limb,
        wherein the computing device is configured to generate a new first stimulation pattern each time the computing device receives the one or more signals associated with the limb from the sensor when the one or more signals indicate a specified activity of the limb, and output the new first stimulation pattern to the first stimulating component in a closed-loop manner.

11. The closed-loop system of claim 10 wherein the predetermined time is between about 5-25 milliseconds.

12. The system of claim 10 wherein the first stimulating component is configured to be worn proximate to the surface of the brain, wherein the first region is a first region of the surface of the brain, wherein the second stimulating component is configured to be worn proximate to the surface of the brain, and wherein the second region is a second region of the surface of the brain.

13. The system of claim 10 wherein the non-transitory computer-executable instructions further include instructions for—
receiving a trigger signal from a sensor; and
outputting the first stimulation pattern when the trigger signal is received.

14. The system of claim 13 wherein the sensor is a movement sensor configured to detect one or more signals associated with movement of a limb of the subject, and wherein the trigger signal comprises one more of the signals associated with the movement of the limb.

15. The system of claim 14, further comprising the movement sensor, wherein the movement sensor is configured to be implanted within and/or worn externally on the limb of the subject.

16. The system of claim 13 wherein the sensor is an activity sensor configured to detect one or more electrical signals associated with muscular activity of the subject, and wherein the trigger signal comprises one more of the signals associated with the muscular activity of the subject.

17. The system of claim 16, further comprising the activity sensor, wherein the activity sensor is configured to be implanted within and/or worn externally on a limb of the subject.

18. A closed-loop system for promoting neuroplasticity in a brain of a subject to improve and/or restore neural function, the closed-loop system comprising:
a sensor configured to be implanted within the subject proximate to a first region of the surface of the brain, wherein the sensor is configured to detect multiple neural signals at the first region of the surface of the brain;
a stimulating component configured to be implanted within the subject proximate to a second region of the surface of the brain implicated in controlling movement of the limb, wherein the stimulating component is configured to receive a stimulation pattern and to stimulate the second region of the surface of the brain based on the stimulation pattern; and
a computing device communicatively coupled to the sensor and the stimulating component, the computing device having a memory containing non-transitory computer-executable instructions and a processor for executing the non-transitory computer-executable instructions contained in the memory, Wherein the non-transitory computer-executable instructions include instructions for—
receiving the detected neural signals from the sensor;
generating the stimulation pattern based on the received neural signals; and
outputting the stimulation pattern to the stimulating component to promote neuroplasticity in the region of the brain by increasing or enhancing activity of neural circuits controlling movement of the limb,
wherein the computing device is configured to generate a new stimulation pattern each time the computing device receives the detected neural signals associated with a specified neural activity and output the new stimulation pattern to the stimulating component in a closed-loop manner.

19. The closed-loop system of claim 18 wherein the neural signals are beta waves having a frequency of between about 15-25 hertz.

20. The system of claim 18 wherein the sensor comprises a first plurality of electrocorticography (ECoG) electrodes, and wherein the stimulating component comprises a second plurality of ECoG electrodes.

21. The system of claim 18 wherein an injured region of the brain is between or functionally associated with the first region and the second region, and wherein stimulating the second region promotes neuroplasticity between the first and second regions.

22. The closed-loop system of claim 18 wherein:
promoting the neuroplasticity in the region of the brain implicated in controlling movement of the limb by the closed-loop system is gradually reduced; and
the closed-loop system is configured to be removed from the subject when sufficient function of the limb has been restored.

* * * * *